United States Patent [19]

Parthasarathy

[11] 3,933,883
[45] Jan. 20, 1976

[54] METHANATION CATALYST AND PROCESS OF USE
[75] Inventor: R. Parthasarathy, Silver Spring, Md.
[73] Assignee: W. R. Grace & Co., New York, N.Y.
[22] Filed: Apr. 14, 1975
[21] Appl. No.: 567,630

[52] U.S. Cl. ... 260/449 M; 260/449.6 R; 252/466 R
[51] Int. Cl.² .......................................... C07C 1/04
[58] Field of Search.. 260/449 M, 449.6 R, 449.6 M

[56] References Cited
UNITED STATES PATENTS

| 3,730,694 | 5/1973 | Wanderlich | 260/449 M UX |
|---|---|---|---|
| 3,876,557 | 4/1975 | Bland | 260/449 M |

FOREIGN PATENTS OR APPLICATIONS

| 1,523,687 | 5/1968 | France | 260/449 M |

Primary Examiner—Howard T. Mars
Attorney, Agent, or Firm—Joseph P. Nigon

[57] ABSTRACT

The methanation reaction, that is, the conversion of carbon monoxide and hydrogen to methane and a water byproduct is conducted at a temperature of 120° to 500°C and a pressure of 100 psig to 2000 psig in the presence of a catalyst consisting of nickel oxide and cobalt oxide in a nickel/cobalt ratio of 1 to 1.5 supported on a high purity alumina support consisting essentially of gamma alumina. The catalyst has a surface area of about 100 to 200 m²/g, an average pore diameter of 100 to 115A and a pore volume of 0.25 to 0.7 cc/g.

5 Claims, No Drawings

METHANATION CATALYST AND PROCESS OF USE

This invention relates to a catalyst for use in the conversion of carbon monoxide and hydrogen to methane. More particularly, this invention relates to alumina supported nickel-cobalt methanation catalysts.

Methanation is a fairly well-known reaction. The reaction consists of the reaction of carbon monoxide and hydrogen in the presence of a catalyst to form methane and a water by-product. Various catalysts have been used for this reaction. Such catalysts include nickel supported on refractory supports, iron-alumina-nickel catalysts, cobalt, iron or nickel supported on fullers earth or silica gel and so on. Generally these catalyst compositions are comprised of large amounts of the active metal or metal oxide. Amounts of 25 to 60 percent by weight of active metal or metal oxide is quite common. However, this is very wasteful of the most expensive component of the catalyst composition. It has been found that a high purity alumina support (greater than 99 percent alumina) having nickel and cobalt present in a nickel/cobalt mole ratio of 1 to 1.5 and at a concentration of 3 to 10 percent by weight metal values, yields a very effective catalyst composition.

It has been observed that there is nickel and cobalt value interaction with an alumina support if the alumina has any substantial amounts of impurities. In order to correct for this, those in the prior art who have used lower purity alumina as the support have used excess amounts of nickel and cobalt values. In such an instance, even though there is interaction with the alumina support, there remains enough nickel and cobalt for reaction catalysis. Such a mode of operation, however, is wasteful of nickel and cobalt. Such catalysts also are initially too active for efficient fluidized bed operation. Furthermore, the impurities present in the catalyst tend to promote side reactions, thereby lowering catalyst selectivity. Since the methanation reaction is so exothermic, such high metals content catalysts tend to fuse into glassy agglomerates. The present catalyst solves this predicament by providing a catalyst which has a low metals loading, but has a sustained long term high activity. The prior art problems are solved by using the present catalyst for fluidized bed operations.

It is therefore a prime object of this invention to set forth an alumina supported nickel-cobalt value fluidized bed catalyst containing about 3 to 10 percent by weight metal values which exhibits high methanation reaction activity and has good stability.

It is a further prime object to set forth an alumina supported nickel-cobalt catalyst which has a nickel/cobalt mole ratio of 1 to 1.5, surface area of 100 to 200 m$^2$/g, an average pore diameter of 100 to 115A and a pore volume of 0.25 to 0.7 cc/g.

It is additionally a prime object of this invention to convert carbon monoxide and hydrogen to methane and a water by-product by contacting said carbon monoxide and hydrogen with the above fluidized bed catalyst at a temperature of 120° to 650°C and a pressure of 100 psig to 2,000 psig.

In more detail, the present invention consists of methanation catalysts for fluidized bed operation. The catalysts consist of nickel and cobalt on a high purity alumina support. The ratio of nickel to cobalt is 1 to 1.5. It is believed that nickel and cobalt in this ratio promote the formation of nickel-cobalt alloys which are responsible for most of the activity of the catalyst. The alumina must be at least 99 percent pure, with only trace amounts of silica, titania and iron oxide permissible. The alumina should be at least 70 percent by weight gamma alumina and be in the form of spheres or ellipsoids, although other shapes can be used. Spherical particles are preferred in fluid bed operations since they have a lower attrition and promote uniform flow characteristics and thereby reduce variations in pressure drop and reduce channeling. The particle size should be in a size range of 40 to 250 microns.

The catalyst is formed by impregnating the alumina particles with nickel and cobalt containing solutions. The impregnation can be conducted separately in either order or the impregnation can be from a nickel and cobalt containing solution. It is preferred that impregnation be from a solution containing both of these metal values, since this will decrease the number of process steps. If separate metal solution impregnation is used, the impregnated support must undergo drying and calcining after each impregnation, while in a co-impregnation there is a single drying and calcination.

The impregnation is conducted by first forming an aqueous solution of the nickel and cobalt metal values. Any water soluble nickel or cobalt salt can be used to form the aqueous solution with the acid salts preferred. Useful acid salts are the nitrates, formates or acetates of nickel and cobalt. The aqueous solution generally contains 1 to 10 percent by weight of nickel and cobalt metal ion. After formation, the nickel-cobalt solution is thoroughly mixed prior to addition to the alumina spheres. If separate impregnations are desired, the nickel and cobalt solutions are formed by the separate dissolution of metal salts in water. Each such separate metal solution contains about 1 to 5 percent by weight of the respective metal ion.

Impregnation is accomplished by adding sufficient nickel and/or cobalt ion solution to create an incipient alumina wetness. This is the case whether the metals are being impregnated separately or as a mixed solution. After impregnation the impregnated mass is dried at 110° to 250°C for 4 to 24 hours and heated at 300° to 800°C for 1 to 10 hours. The catalyst at this point is in a condition for reduction of the cobalt and nickel to the metallic form and use, but in a preferred embodiment the spheres are elutiated with air to remove any catalyst fines.

In the embodiment of separate nickel and cobalt ion impregnation, the impregnated alumina is dried at 110° to 250°C for 4 to 24 hours and heated at 300° to 800°C for 1 to 10 hours between the separate metal ion impregnations. The drying and the heating prevents the removal of the first impregnated metal by the solution of the second metal solution. As hereinabove pointed out, the metal ion impregnations may be in either order, that is, either the nickel ion solution or the cobalt ion solution may be impregnated first into the alumina support. However, it is preferred that the impregnation be a co-impregnation of the nickel and cobalt value containing solutions.

The reduction of the nickel and cobalt metal oxides to metals consists of contacting the calcined catalyst with hydrogen at a temperature of 250° to 600°C for 1 to 20 hours. Preferably, before contact with hydrogen, the catalyst is contacted with nitrogen to remove air.

The final catalyst formulation should contain about 3 to 10 percent by weight of nickel and cobalt calculated as the metal. The atomic ratio of nickel to cobalt is 1 to 1.5. The particle size of the catalyst is 40 to 250 microns. The BET surface area of the catalyst is about 100 to 200 m²/g, and preferably 125 to 175 m²/g. The pore diameter range is 35 to 200 A and preferably 50 to 180 A. The nitrogen pore volume of the catalyst is 0.25 to 0.7 cc/g, and preferably 0.3 to 0.55 cc/g.

In use the catalyst is placed in a fluidized bed reactor in sufficient quantity to provide the desired pressure drop during fluidization. A gas such as a coal gas is fed to the bed at a pressure of 100 to 2,000 psig with a temperature of 120° to 650°C being maintained in the reactor. The feed gas hourly space velocity flow rate is 500 to 3,000 hr⁻¹. The fluidized zone may range from 2 to 20 feet. The carbon monoxide and hydrogen components of the coal gas react to form methane and a water by-product. The reaction is essentially $$CO + 3 H_2 \rightarrow CH_4 + H_2O.$$

The methane content of the coal gas feed is not affected by contact with this catalyst at reaction conditions. Coal gas can contain about 20 percent methane.

The following examples further amplify the preferred embodiments of the invention.

EXAMPLE 1

A spherical boehmite alumina of greater than 99 percent purity, a BET surface area of 160 m²/g and nitrogen pore volume of 0.4 to 0.5 cc/g was calcined for 3 hours at 540°C to convert the boehmite alumina to gamma alumina. The calcined alumina spheres were then sized to through a 120 U.S. mesh screen and on a 325 mesh screen.

A mixed nickel and cobalt ion solution was formed by dissolving 58 g of nickel nitrate hexahydrate and 58 g of cobalt nitrate hexahydrate in 141 g of water. After stirring to complete dissolution, amounts of the mixed metal solution are added to 300 g of the gamma alumina spheres to incipient wetness of the spheres. The impregnated alumina spheres are then dried at 150°C for 16 hours and calcined for 3 hours at 540°C. The calcined spheres were then elutriated for 0.5 hour to remove any dust fines. The spheres were placed in a stirred tank laboratory reactor, and the reactor was sealed and pressurized with nitrogen to 350 psig. The reactor was heated to a temperature of 290°C, and hydrogen was then substituted for the nitrogen. The temperature was further raised to 470°C. At this temperature the cobalt and nickel were converted to the metal; the treatment was continued at this temperature for 4 hours.

EXAMPLE 2

A commercially available hydrous alumina powder with low crystallinity was calcined for 3 hours at 593°C and characterized. A catalyst was prepared using this powder following the procedure described in Example 1. The properties of the catalysts of Examples 1 and 2 are in the following Tables.

TABLE 1

| Properties of Catalyst Supports | Example 1 | Example 2 |
|---|---|---|
| Calcination Temperature | 540°C | 593°C |
| Surface Area, m²/g | 160 | 209 |
| Nitrogen Pore Volume, cm³/g | 0.4–0.5 | 0.85 |

TABLE 2

| Properties of Catalyst Supports | Example 1 | Example 2 |
|---|---|---|
| % Nickel (as Ni) | 5.10 | 4.6 |
| % Cobalt (as Co) | 3.73 | 4.12 |
| Surface Area, m²/g | 155 | 299 |
| Water Pore Volume, cm³/g | 0.58 | 0.77 |

EXAMPLE 3

A packed bed catalytic reactor, ½ inch inside diameter and 18 inches long, was used to test the stability of the catalysts of Examples 1 and 2. A synthetic gas mixture similar to a product gas from coal gasifiers, containing 20 percent CO, 60 percent H₂ and 20 percent CH₄, was fed to the reactor under 1000 pounds pressure and the conversions measured at successively higher temperatures from 425° to 600°C over a period of about 250 hours. The catalysts of Examples 1 and 2 both showed excellent initial activity, giving conversions of 95 percent theoretical. When the temperatures were returned to about 425°C it was found that the catalyst of Example 1 had retained all of its activity, while the catalyst of Example 2 had a conversion of about 47 percent of theoretical based on carbon monoxide. A second heating cycle similar to the first was made, and it was found that the catalyst of Example 2 had lost activity to the extent that it was now converting less than 20 percent of the incoming carbon monoxide. However, no change was observed in the preferred catalyst of Example I. This illustrates the uniqueness of the preferred catalyst base used in Example 1. The catalyst of Example 1 was operated for a total of 660 hours without any loss in activity measured by the conversion of feed gas carbon monoxide.

EXAMPLE 4

The catalyst described in Example 1 was charged to a fluidized bed unit which was operated under the following conditions:

| | |
|---|---|
| Feed Composition: | 20% CO |
| | 60% H₂ |
| Balance | CH₄ |
| Reactor Temperature: | 800°F |
| Reactor Pressure: | 70 atm |
| Feed Gas Hourly Space Velocity: | 2000 hr⁻¹ |

More than 80 percent of the carbon monoxice and hydrogen in the feed gas was converted to methane, with the product gas containing greater than 80 mole percent methane.

The catalyst operated for over 660 hours continuously without adverse carbon deposition and resultant loss in activity. A similar catalyst prepared on a low purity alumina (at 98 percent purity, with impurities such as SO₄, Na₂O and silica at 2 percent) lost its activity rapidly in less than 100 hours.

What is claimed is:

1. A method for converting a feed gas stream containing principally carbon monoxide, hydrogen and methane to a product gas stream containing essentially completely methane, comprising passing said feed gas stream in fluidized contact with a catalyst consisting of an alumina support having a purity of more than 99 percent by weight alumina, of which at least 70 percent by weight is present as gamma alumina and impregnated with nickel and cobalt in a nickel to cobalt atomic ratio of 1 to 1.5 and containing about 3 to 10 percent by weight metal values, said catalyst having a surface area of about 100 to 200 m²/g, pores in a pore diameter range of 35 to 200A, with an average pore diameter of 100 to 115A and a pore volume of 0.25 to 0.7 cc/g; at a pressure of 100 to 2,000 psig and at a temperature of 120° to 650°C.

2. A method as in claim 1 wherein the flow rate of said feed gas is 500 to 3000 hourly space velocity.

3. A method as in claim 1 wherein said catalyst has a nickel to cobalt atomic ratio of 1.10 to 1.30, a surface area of 125 to 175 m²/g, a pore diameter range of 50 to 180A and a pore volume of 0.3 to 0.55 cc/g.

4. A method as in claim 2 wherein said catalyst consists of spherical particles of 40 to 250 microns.

5. A method as in claim 4 wherein the flow rate of said feed gas is 500 to 3,000 hourly space velocity.

* * * * *